United States Patent
Luo

(10) Patent No.: US 12,169,272 B2
(45) Date of Patent: Dec. 17, 2024

(54) LINE TUBE ADAPTER ASSEMBLY AND ENDOSCOPE

(71) Applicant: AUTEL INTELLIGENT TECHNOLOGY CORP., LTD., Guangdong (CN)

(72) Inventor: Wenhui Luo, Guangdong (CN)

(73) Assignee: Autel Intelligent Technology Corp., Ltd., Shenzhen (CN)

(*) Notice: Subject to any disclaimer, the term of this patent is extended or adjusted under 35 U.S.C. 154(b) by 363 days.

(21) Appl. No.: 17/651,980

(22) Filed: Feb. 22, 2022

(65) Prior Publication Data

US 2022/0171179 A1    Jun. 2, 2022

Related U.S. Application Data

(63) Continuation of application No. PCT/CN2020/113581, filed on Sep. 4, 2020.

(30) Foreign Application Priority Data

Sep. 6, 2019 (CN) .......................... 201910842095.4

(51) Int. Cl.
*H01R 13/72* (2006.01)
*G02B 23/24* (2006.01)
*H01R 13/516* (2006.01)

(52) U.S. Cl.
CPC ......... *G02B 23/2476* (2013.01); *H01R 13/72* (2013.01); *H01R 13/516* (2013.01)

(58) Field of Classification Search
CPC .... G02B 23/2476; G02B 23/24; H01R 13/72; H01R 13/516; H01R 2201/12;
(Continued)

(56) References Cited

U.S. PATENT DOCUMENTS

| 3,219,961 A | 11/1965 | Bailey et al. |
| 5,683,270 A | 11/1997 | Warislohner |

(Continued)

FOREIGN PATENT DOCUMENTS

| CN | 201986304 U | 9/2011 |
| CN | 104864299 A | 8/2015 |

(Continued)

OTHER PUBLICATIONS

The Extended European Search Report dated Aug. 1, 2022; Application. No. 20861370.3.

(Continued)

*Primary Examiner* — Abdullah A Riyami
*Assistant Examiner* — Nelson R. Burgos-Guntin
(74) *Attorney, Agent, or Firm* — Andrew C. Cheng

(57) ABSTRACT

A line tube adapter assembly and an endoscope. The line tube adapter assembly comprises: a housing 100 formed with an accommodation cavity 111; a connector 200 comprising a base 210 and a transmission line 220, the base 200 being accommodated in the accommodation cavity 111, and the transmission line 220 being connected to one end of the base 210; a line storage device 300 accommodated in the accommodation cavity 111, the line storage device 300 being formed with an accommodation space 310, and the accommodation space 310 being configured to accommodate part of the transmission line 222; and a line tube 400 arranged at the end of the line storage device 300 away from the base 210, the line tube 400 being connected to the housing 100. The line tube adapter assembly comprises the line storage device 300, and the overlong transmission line 220 can be accommodated in the accommodation space 310 of the line storage device 300 in a bending and folding manner, so that the overlong transmission line 220 is prevented from being accommodated in the housing 100 dis- (Continued)

orderly, and the transmission line 220 is further prevented from being extruded and damaged in a matching process of the housing 100 and the line tube 400.

12 Claims, 3 Drawing Sheets

(58) Field of Classification Search
CPC ..... H01R 13/73; H01R 31/06; A61B 1/00114; A61B 1/00124
See application file for complete search history.

(56) References Cited

U.S. PATENT DOCUMENTS

| | | | |
|---|---|---|---|
| 9,966,696 B2 | 5/2018 | Cheng | |
| 2007/0260120 A1* | 11/2007 | Otawara | G02B 23/2476 600/156 |
| 2008/0064928 A1* | 3/2008 | Otawara | A61B 1/051 600/129 |
| 2009/0259101 A1* | 10/2009 | Unsai | A61B 1/05 600/110 |
| 2010/0004509 A1* | 1/2010 | Naito | A61B 1/00133 600/141 |
| 2011/0034769 A1* | 2/2011 | Adair | H04N 23/54 600/110 |
| 2012/0329312 A1 | 12/2012 | Que et al. | |
| 2013/0310644 A1* | 11/2013 | Ichimura | A61B 1/051 600/109 |
| 2014/0094656 A1 | 4/2014 | Matsukawa et al. | |
| 2015/0230693 A1* | 8/2015 | Kubo | H04N 23/56 174/261 |
| 2016/0089000 A1* | 3/2016 | Hara | A61B 1/00112 600/112 |
| 2017/0181609 A1 | 6/2017 | Tanii | |
| 2018/0090880 A1 | 3/2018 | Cheng | |
| 2018/0185591 A1* | 7/2018 | Cha | A61B 1/00087 |
| 2018/0206713 A1* | 7/2018 | Hayashi | G02B 23/2461 |
| 2018/0228357 A1* | 8/2018 | Fujii | A61B 1/127 |
| 2018/0228557 A1* | 8/2018 | Darisse | A61B 1/0057 |
| 2018/0249899 A1* | 9/2018 | Ouchi | A61B 17/2909 |
| 2018/0256016 A1* | 9/2018 | Amano | A61B 1/00027 |
| 2018/0263469 A1* | 9/2018 | Okaniwa | G02B 23/24 |
| 2018/0280046 A1* | 10/2018 | Ngo-Chu | A61B 17/29 |
| 2018/0310802 A1* | 11/2018 | Gilreath | A61B 1/0615 |
| 2018/0375236 A1* | 12/2018 | Arakawa | H01R 12/732 |
| 2022/0171179 A1* | 6/2022 | Luo | A61B 1/00114 |

FOREIGN PATENT DOCUMENTS

| | | |
|---|---|---|
| CN | 105222026 A | 1/2016 |
| CN | 206135166 U | 4/2017 |
| CN | 106610524 A | 5/2017 |
| CN | 207134515 U | 3/2018 |
| CN | 207505339 U | 6/2018 |
| CN | 207947456 U | 10/2018 |
| CN | 108802910 A | 11/2018 |
| CN | 109254394 A | 1/2019 |
| CN | 208508090 U | 2/2019 |
| CN | 209016373 U | 6/2019 |
| CN | 110444978 A | 11/2019 |
| CN | 210326406 U | 4/2020 |
| KR | 20140076207 A | 6/2014 |
| WO | 2017067491 A1 | 4/2017 |

OTHER PUBLICATIONS

International search report mailed Dec. 11, 2020; PCT/CN2020/113581.
First office action of CN patent application of No. 201910842095.4 issued on Feb. 23, 2024.
Search report of CN patent application of No. 201910842095.4 issued on Feb. 23, 2024.

* cited by examiner

LINE TUBE ADAPTER ASSEMBLY AND ENDOSCOPE

CROSS REFERENCE

The present application claims priority to the Chinese Patent Application No. 201910842095.4 entitled "line tube adapter assembly and endoscope" filed on Sep. 6, 2019, to the China National Intellectual Property Administration, the entire contents of which are incorporated herein by reference.

TECHNICAL FIELD

The present application relates to the technical field of communication connections, and more particularly to a line tube adapter assembly and an endoscope.

BACKGROUND ART

Industrial or medical equipment often requires the communication or charging and discharging with external equipment via a communication line. One end of the communication line away from the industrial or medical device is provided with a line tube adapter. Such line tube adapters generally include a housing, a line tube, and a strip line connector accommodated between the housing and the line tube. The strip line connector comprises a base, a transmission line, and a communication port. The base is accommodated in the housing and fixed to the housing, the transmission line and the communication port are respectively connected to two ends of the base, one end of the transmission line away from the base extends from the housing to one end of the line tube away from the housing and is connected to the above-mentioned industrial or medical equipment, and the communication port is configured to connect to the above-mentioned external equipment to realize a communication or charging and discharging process with the external equipment.

However, the inventor of the present invention has found in the course of carrying out the present invention that: at present, the shell and the line tube of the line tube adapter are sometimes tightly fitted and fixed by means of stamping; since the transmission line is overlong and is in a disordered state both in the shell and the line tube, in the process of stamping and tightly fitting the shell and the line tube, the shell or the line tube is easily squeezed strongly against the transmission line to cause the transmission line to be damaged, thereby affecting the normal communication connection between the above-mentioned industrial or medical equipment and the external equipment, resulting in low user satisfaction degree.

SUMMARY OF THE INVENTION

Embodiments of the present invention are intended to provide a line tube adapter assembly and an endoscope to solve the present technical problem that a shell of a line tube adapter and the line tube may easily damage a transmission line in a matching process.

The present invention solves the technical problem thereof by using the following technical solutions.

A line tube adapter assembly, comprises:
a housing provided with an accommodation cavity;
a connector comprising a base and a transmission line, wherein the base is accommodated in the accommodation cavity, and the transmission line is connected to one end of the base;
a line storage device accommodated in the accommodation cavity, wherein the line storage device is provided with an accommodation space configured to accommodate part of the transmission line;
and a line tube provided at one end of the line storage device away from the base, the line tube being connected to the housing.

As a further improvement of the above-mentioned technical solution, the accommodation space is a through-hole extending through the line storage device from one end close to the base to one end away from the base.

As a further improvement of the above-mentioned technical solution, an outer wall of the line storage device is further provided with a side opening communicating with the accommodation space;
the accommodation space always communicates with the side opening from one end close to the base to one end away from the base.

As a further improvement of the above-mentioned technical solution, the line storage device is integrally formed with the base.

As a further improvement of the above-mentioned technical solution, the line tube adapter assembly further comprises a first limiting part and a second limiting part adapted to the first limiting part, wherein the first limiting part is located in the accommodation cavity and provided on an inner wall of the housing, and the second limiting part is provided on an outer wall of the base, the first limiting part and the second limiting part matching to circumferentially fix the connector and the housing.

As a further improvement of the above-mentioned technical solution, the inner wall of the housing is provided with a first plane, the first plane being the first limiting part, and the outer wall of the base is provided with a second plane, the second plane being the second limiting part, and the first plane is fitted with the second plane.

As a further improvement of the above-mentioned technical solution, the first limiting part is a limiting protrusion extending from the inner wall of the housing to the center of the housing, the second limiting part is a limiting groove extending from the outer wall of the base to the center of the base and adapted to the limiting protrusion, and circumferential fixing is achieved between the housing and the connector through the matching of the limiting protrusion and the limiting groove; alternatively,
the first limiting part is a limiting groove extending from the inner wall of the housing to a direction away from the center of the housing, the second limiting part is a limiting protrusion extending from the outer wall of the base to a direction away from the center of the base and adapted to the limiting groove, and circumferential fixing is achieved between the housing and the connector through the matching of the limiting groove and the limiting protrusion.

As a further improvement of the above-mentioned technical solution, the line tube adapter assembly of claim 1 further comprises a third limiting part, and a fourth limiting part adapted to the third limiting part, wherein the third limiting part is located in the accommodation cavity and is provided on an inner wall of the housing, the fourth limiting part is provided on an outer wall of the line storage device, and the third limiting part and the fourth limiting part match to circumferentially fix the line storage device and the housing.

As a further improvement of the above-mentioned technical solution, the inner wall of the housing is provided with a third plane, the third plane being the third limiting part, and the outer wall of the line storage device is provided with a fourth plane, the fourth plane being the fourth limiting part, and the third plane is fitted with the fourth plane.

As a further improvement of the above-mentioned technical solution, the accommodation space is a through-hole extending through the line storage device from one end close to the base to one end away from the base;

the outer wall of the line storage device is further provided with a side opening communicating with the accommodation space, and the accommodation space always communicates with the side opening from one end close to the base to one end away from the base;

the side opening divides the fourth plane into two parts.

As a further improvement of the above-mentioned technical solution, the connector further comprises a communication port provided at one end of the base away from the transmission line, the communication port being connected to the transmission line.

As a further improvement of the above-mentioned technical solution, the housing is threadedly connected to the line tube.

As a further improvement of the above-mentioned technical solution, the inner side wall of the housing is provided with a centrally extending flange, one end of the base away from the transmission line abutting against the flange, one end of the base away from the flange abutting against or being fixed to the line storage device, and one end of the line tube extending into the accommodation cavity, abutting against the line storage device, and being threadedly connected to the housing.

The present invention solves the technical problem thereof by further using the following technical solutions.

An endoscope comprises an endoscope body, and the above-mentioned line tube adapter assembly, one end of the transmission line away from the base being connected to the endoscope body.

The advantageous effects of the present invention are as follows.

An embodiment of the present invention provides a line tube adapter assembly comprising a housing, a connector, a line storage device, and a line tube, wherein the connector comprises a base and a transmission line connected to the base, the base, and the line storage device are both accommodated in an accommodation cavity of the housing, and the line storage device is provided with an accommodation space.

Compared with the current line tube adapters, the line tube adapter assembly provided by embodiments of the present invention further comprises a line storage device, and the overlong transmission line can be accommodated in the accommodation space of the line storage device in a bending and folding manner, so that the overlong transmission line is prevented from being accommodated in the housing disorderly, and the transmission line is further prevented from being extruded and damaged in a matching process of the housing and the line tube.

BRIEF DESCRIPTION OF THE DRAWINGS

One or more embodiments are illustrated by way of examples with the accompanying drawings. The illustrative examples are not to be construed as limiting the embodiments. In the drawings, elements having the same reference numeral designations represent like elements, and unless otherwise specified, the drawings are not to scale.

DETAILED DESCRIPTION OF THE INVENTION

In order that the present invention may be readily understood, a more particular description of the invention will be rendered by reference to specific embodiments and the accompanying drawings. It should be noted that when an element is referred to as being "secured"/"fixed" to another element, it can be directly on the other element or one or more intermediate elements may be present between the elements. When one element is referred to as being "connected" to another element, it can be directly connected to the other element or one or more intermediate elements may be present between the elements. The terms "vertical", "horizontal", "left", "right", "inner", "outer", and the like are used herein for descriptive purposes only.

Unless defined otherwise, all technical and scientific terms used in the description have the same meaning as commonly understood by one of ordinary skill in the art to which this invention belongs. The terms used in the description of the present invention are for the purpose of describing specific embodiments only and are not intended to be limiting of the present invention. As used in the description, the term "and/or" includes any and all combinations of one or more of the associated listed items.

Further, the technical features involved in various embodiments of the present invention described below can be combined as long as they do not conflict with each other.

In this description, "mounting" includes welding, screwing, clamping, gluing, etc. to fix or restrain a certain element or device in a specific position or place. The element or device may either be fixed in a specific position or place, or may be movable within a limited range. The element or device may or may not be detachable after being fixed or limited in the specific position or place, and is not limited in the embodiments of the present invention.

Figure 1:
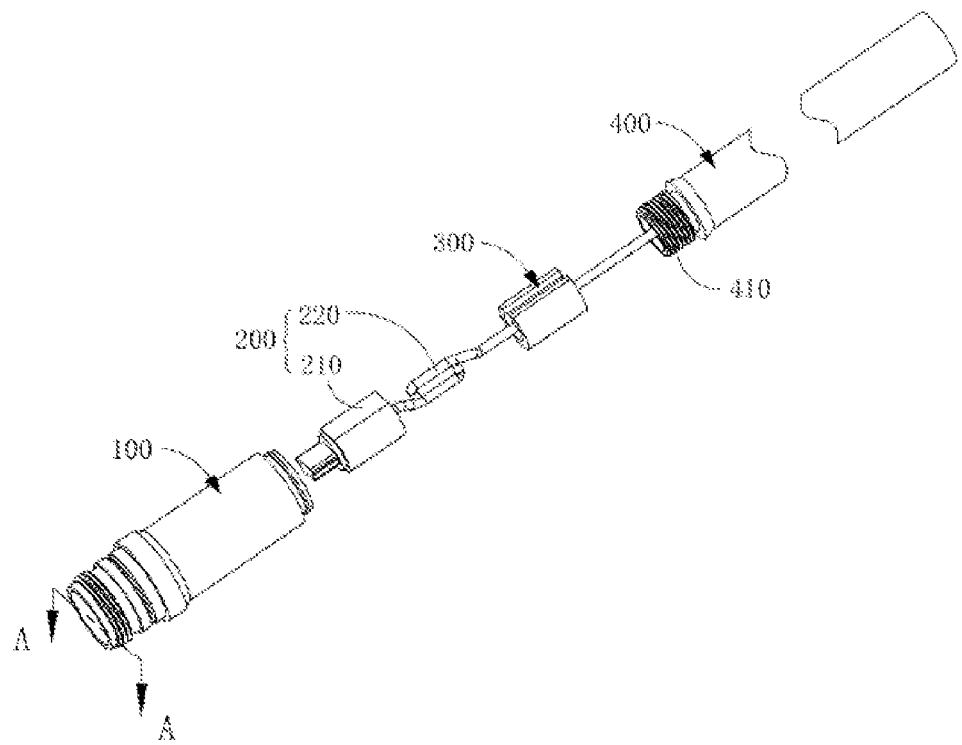
FIG. 1 is an exploded view of a line tube adapter assembly in one direction provided by an embodiment of the present invention.
Figure 2:
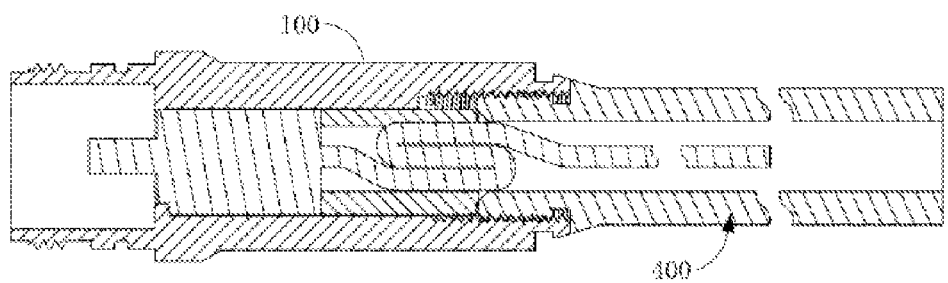
FIG. 2 is a schematic sectional view of the line tube adapter assembly of FIG. 1 taken along line A-A.

Referring to FIGS. 1 to 2 that respectively showing an exploded view of a line tube adapter assembly in one direction provided by an embodiment of the present invention, and a schematic sectional view taken along line A-A, the line tube adapter assembly includes a housing 100, a connector 200, a line storage device 300, and a line tube 400. The connector 200 includes a base 210 and a transmission line 220; the base 210 and the line storage device 300 are both accommodated in the housing 100; one end of the base 210 abuts against the housing 100, and the other end abuts against the line storage device 300; the transmission line 220 is connected to one end of the base 210 close to the line storage device 300; one end of the line tube 400 extends into the interior of the housing 100 and abuts against the line storage device 300; and at the same time, one end of the line tube 400 extending into the housing 100 is fixedly connected to the housing 100.

Figure 3:
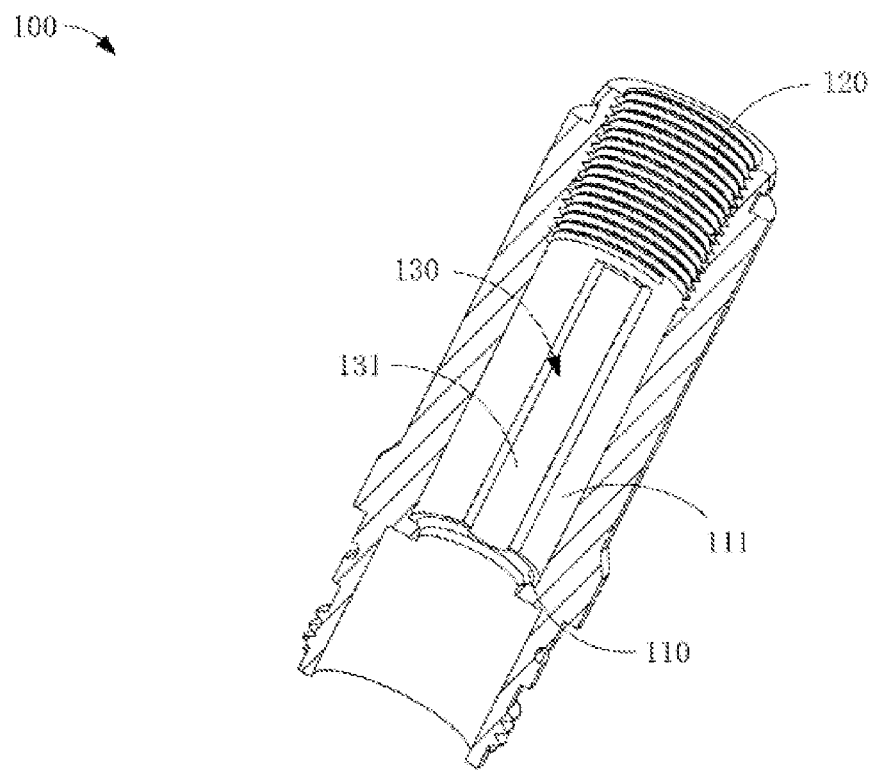
FIG. 3 is a schematic sectional view of a housing of FIG. 1 in one direction.

With regard to the above-mentioned housing 100, reference is made to FIG. 3, which shows a schematic sectional view of the housing 100 in one direction. And in conjunction with FIGS. 1 and 2, the housing 100 has an overall hollow cylindrical structure, the inner side wall thereof is provided with a flange 110 formed by extending toward the center, and the flange 110 has a ring shape. An accommodation cavity 111 for accommodating the base 210 and the line storage device 300 is enclosed between the flange 110 and the housing 100. One end of the housing 100 is provided with an internal thread 120, which is located in the above-mentioned accommodation cavity 111 and is used for connecting with an external thread on the line tube 400.

Figure 4:
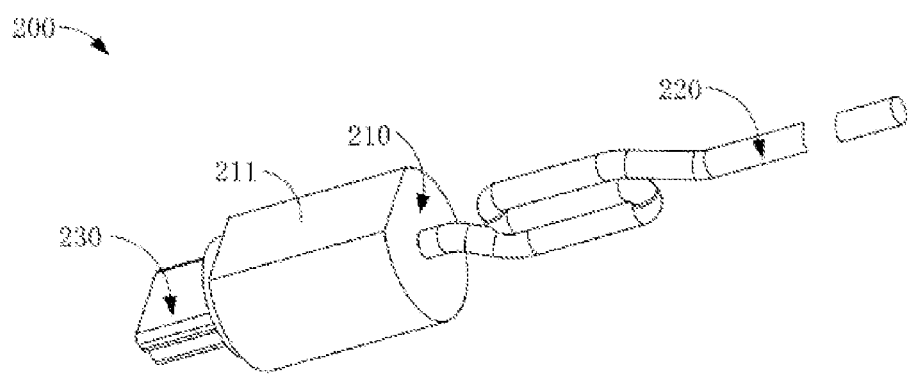
FIG. 4 is a schematic perspective view of a connector of FIG. 1 in one direction.

With respect to the above-mentioned connector 200, the reference is made to FIG. 4, which shows a schematic perspective view of the connector 200 in one direction. In conjunction with FIGS. 1-3, the connector 200 specifically includes a base 210, a transmission line 220, and a communication port 230. The base 210 is accommodated in the housing 100 in an approximately cylindrical shape adapted to the inner wall of the housing 100, and the transmission line 220 and the communication port 230 are respectively provided at both ends of the base 210 in the axial direction of the base 210. One end of the base 210 away from the transmission line 220 abuts against the above-mentioned flange 110, and the other end abuts against the line storage device 300. One end of the transmission line 220 is connected to the base 210 and the other end extends away from the flange 110 and into the line tube 400. The communication port 230 for connecting with external equipment passes through the flange 110 and is connected with the transmission line 220.

Further, in order to prevent the transmission line 220 from being twisted in the housing 100 or the line tube 400 due to the circumferential rotation of the assembled connector 200 inside the housing, which makes the transmission line 220 easily damaged by overwork, and to prevent the communication port 230 from being randomly rotated, the present line tube adapter assembly further includes a first limiting part and a second limiting part adapted to the first limiting part, wherein the first limiting part is located in the accommodation cavity and is provided on the inner wall of the housing 100, and the second limiting part is provided on the outer wall of the base 210, and the first limiting part and the second limiting part cooperate to fix the connector 200 and the housing 100 in the circumferential direction.

Specifically, referring to FIGS. 3 and 4, a limiting protrusion 130 is provided on the inner wall of the housing 100 between the flange 110 and the internal thread 130. The end face of one end of the limiting protrusion 130 near the center of the housing 100 is a first plane 131, and the first plane 131 is parallel to the axis of the housing 100, and the first plane 131 is the above-mentioned first limiting part. Correspondingly, the outer wall of the base 210 is provided with a second plane 211, and the second plane 211 is parallel to the axis of the base 210, and the second plane 211 is the above-mentioned second limiting part. The distance between the first plane 131 and the axis of the housing 100 is equal to the distance between the second plane 211 and the axis of the base 210. When the connector 200 is loaded into the accommodation cavity 111, the second plane 211 is fitted with the first plane 131, and the remaining surface of the inner wall of the housing 100 is adapted and fitted with the remaining surface of the outer wall of the base 210. It is to be understood that the first plane 131 of the embodiment is indirectly formed on the inner wall of the housing 100 through the limiting protrusion 130. However, in other embodiments of the present invention, the first plane may be formed directly on the inner wall of the housing 100, for example, the inner wall of the housing 100 having a D-shape.

It should be understood that although the first limiting part and the second limiting part in the above-mentioned embodiments are both limiting planes, the present invention is not limited thereto; as long as the above-mentioned first limiting part and the second limiting part cooperate together so as to fix the installed connector 200 and housing 100 in the circumferential direction, it will do; for example: in some embodiments of the present invention, the first limiting part is a limiting protrusion extending from the inner wall of the housing to the center of the housing, and the second limiting part is a limiting groove extending from the outer wall of the base to the center of the base, wherein the limiting groove is adapted to the limiting protrusion, and the housing and the connector are circumferentially fixed by the matching of the limiting protrusion and the limiting groove; in further embodiments of the present invention, the first limiting part is a limiting groove extending from the inner wall of the housing towards a direction away from the center of the housing, and the second limiting part is a limiting protrusion extending from the outer wall of the base towards a direction away from the center of the base, wherein the limiting protrusion is adapted to the limiting groove, and the housing and the connector are circumferentially fixed by the matching of the limiting groove and the limiting protrusion.

Figure 5:
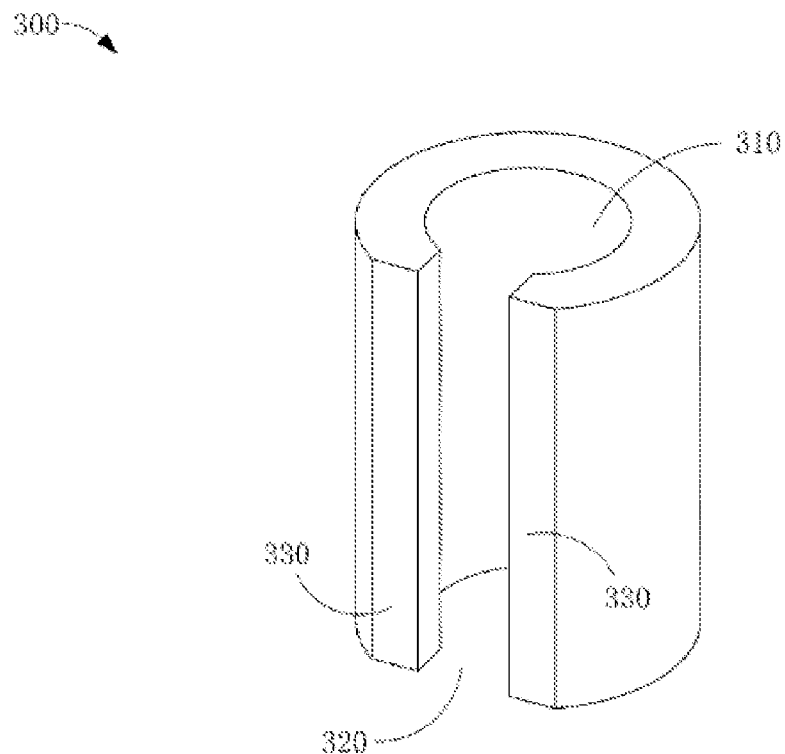
FIG. 5 is a schematic perspective view of a line storage device of FIG. 1 in one direction.

With regard to the line storage device 300, the reference is made to FIG. 5, which shows a schematic perspective view of the line storage device 300 in one direction. In conjunction with FIGS. 1 to 4 at the same time, the line storage device 300 has an overall cylindrical structure, which is accommodated in the accommodation cavity 111 in parallel, and one end of the line storage device 300 abuts against one end of the base 210 away from the flange 110, and the other end abuts against one end of the line tube 400 extending into the housing 100. The line storage device 300 is provided with an accommodation space 310 in the form of a through-hole extending through the line storage device 300 from one end close to the base 210 to one end away from the base 210. The outer wall of the line storage device 300 is further provided with a side opening 320 communicating with the accommodation space 310, the side opening 320 extending from one end close to the base to one end away from the base. The accommodation space 310 always communicates with the side opening 320 from one end close to the base 210 to one end away from the base 210. The overlong transmission line 220 in the housing 100 and the line tube 400 can be accommodated in the accommodation space 310 of the line storage device 300 by bending and folding (as shown in FIG. 4), and the side opening 320 is provided to facilitate placing the bent and folded transmission line 220 in the accommodation space 310. It is to be understood that in other embodiments of the present invention, the line storage device 300 may also be provided without a side opening, i.e. the line storage device 300 has an O-shape cross section parallel to the end face, and correspondingly, the bent and folded transmission line is accommodated in the line storage device 300 through the end part of the accommodation space 310.

Further, in order to prevent the transmission line 220 from being twisted in the accommodation cavity 111 or the line tube 400 due to the circumferential rotation of the assembled line storage device 300 inside the housing 100, which makes the transmission line 220 easily damaged by overwork, the present line tube adapter assembly further comprises a third limiting part and a fourth limiting part adapted to the third limiting part, wherein the third limiting part is located in the accommodation cavity 111 and is provided on the inner wall of the housing 100, the fourth limiting part is provided on the outer wall of the line storage device 300, and the third limiting part and the fourth limiting part cooperate together to circumferentially fix the line storage device 300 and the housing 100.

Specifically, referring to FIGS. 3 and 5, and in conjunction with FIGS. 1, 2, and 4, the inner wall of the housing 100 is provided with a third plane, and the third plane is parallel to the axis of the housing 100, and the third plane is the above-mentioned third limiting part. In this embodiment, the third plane is the above-mentioned first plane 131. Accordingly, the outer wall of the line storage device 300 is provided with a fourth plane 330, and the fourth plane 330 is parallel to the axis of the line storage device 300, and the fourth plane 330 is the above-mentioned fourth limiting part. The distance between the third plane and the axis of the housing 100 is equal to the distance between the fourth plane 330 and the axis of the line storage device 300. In the process of loading the line storage device 300 into the housing 100, the above-mentioned fourth plane 330 is fitted with the third plane, and the remaining surface of the inner wall of the housing 100 is adapted and fitted with the remaining surface of the outer wall of the line storage device 300. It will be understood that in other embodiments of the present invention, the third plane and the first plane 131 may also be two different planes.

Preferably, the fourth plane 330 is provided at the side opening 320 of the line storage device 300, and the side opening 320 divides the fourth plane 330 into two parts. The fourth plane 330, after being fitted with the third plane, can block the transmission line 220 accommodated in the line storage device 300 from moving out of the line storage device 300 through the side opening 320. With regard to the above-mentioned line tube 400, referring to FIGS. 1 and 2, the line tube 400 has an overall cylindrical structure, one end of which extends into the accommodation cavity 111 and abuts against one end of the line storage device 300 away from the base 210. One end of the line tube 400 abutting against the line storage device 300 is provided with an external thread 410, and the line tube 400 is fixedly connected to the housing 100 through the external thread 410 and the above-mentioned internal thread 120. It should be understood that in other embodiments of the present invention, the external thread may also be provided on the housing, and correspondingly, the internal thread may be provided on the line tube, and the two may be fixed by matching the internal thread and external thread; in addition, the line tube 400 may be fixedly connected to the housing 100 via a snap connection or the like.

The line tube adapter in the current market includes a housing, a connector, and a line tube. There are generally two fixing modes between the housing and the line tube, wherein one is to stamp the housing and the line tube into a coaxial close-fitting fixing through die stamping, and the other is to glue-fix the housing and the line tube through an adhesive such as glue. The mode of close-fitting fixing by stamping easily causes the housing or the line tube to extrude the transmission line to damage the transmission line; however, with regard to the glue-fixing mode, as time goes by, the product gradually ages, and the adhesive will fall off, and the line tube and the housing will separate, which will lead to the damage of the line tube adapter.

However, the present invention provides a line tube adapter assembly, including a housing 100, a connector 200, a line storage device 300, and a line tube 400. On the one hand, the arrangement of the line storage device 300 can accommodate an overlong transmission line, so as to avoid damaging the transmission line during the assembly of the housing 100 and the line tube 400; and on the other hand, both ends of the line storage device 300 abut against the base of the connector 200 and the end part of the line tube 400, respectively, so that the connector 200 is fixed to the housing 100, and at the same time, one axial force is applied to the line tube 400 so that the axial force between the line tube 400 and the housing 100 is sufficiently large, thereby enhancing the self-locking effect of the threaded connection of the line tube 400 and the housing 100. Since the line tube adapter is not fixed by bonding, the line tube 400 of the line tube adapter will not separate from the housing 100 by product aging. In addition, the arrangement of a threaded connection between the line tube 400 and the housing 100 also facilitates the disassembly and assembly of the two, thereby facilitating the maintenance of the line tube adapter device.

Figure 6:
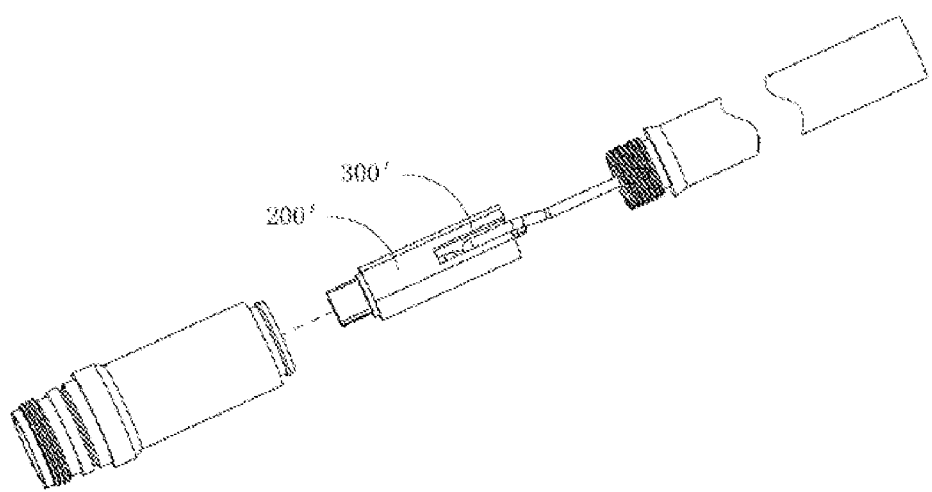
FIG. 6 is a schematic perspective view of a line tube adapter assembly in one direction provided by another embodiment of the present invention.

Referring to FIG. 6, there is shown a schematic perspective view of a line tube adapter assembly in one direction provided by another embodiment of the present invention. In conjunction with FIGS. 1-5 at the same time, the line tube adapter assembly of the present embodiment is generally the same as the line tube adapter assembly of the above-mentioned embodiment, with the major differences lying in that: the connector 200 and the line storage device 300 in the first embodiment are independently arranged; however, the connector 200' and the line storage device 300' in the present embodiment are integrally formed and arranged, namely: one end of the line storage device 300' close to the connector 200' is fixedly connected to the base of the connector 200'. The integral arrangement of the connector 200' and the line storage device 300' facilitates the overall disassembly and assembly of the connector 200' and the line storage device 300', and the disassembly and assembly process of the line tube adapter assembly is simpler and more convenient.

It is to be understood that the line storage device 300' in the second embodiment may not be arranged with the above-mentioned side opening, that is, the cross section of the line storage device 300' parallel to the end face is O-shaped; the fourth plane may not be arranged at the side opening.

Based on the same inventive concept, the present invention also provides an endoscope, including an endoscope body (not shown) and the above-mentioned line tube adapter assembly. Referring to FIGS. 1 to 6, one end of the transmission line away from the flange is connected to the endoscope body. The endoscope may be applied in the industrial field or medical field.

According to the present invention, there is provided an endoscope line tube adapter assembly, including the above-mentioned line storage device. On the one hand, the line storage device is configured to accommodate an overlong transmission line, so that the transmission line connected to the above-mentioned endoscope body is not easily damaged; on the other hand, both ends of the line storage device respectively abut against the base of the connector and the end part of the line tube, so that the connector is fixed to the housing, and at the same time, one axial force is applied to the line tube, so that the axial force between the line tube and the housing is sufficiently large, thereby enhancing the self-locking effect of the threaded connection of the line tube and the housing. Since the line tube adapter is not fixed by bonding, the line tube and the housing of the line tube adapter in the endoscope will not separate by product aging.

Finally, it should be noted that: the above embodiments are merely illustrative of the technical solutions of the present invention, rather than limiting the same; combinations of technical features in the above embodiments or in different embodiments are also possible within the concept of the invention, the steps may be implemented in any order, and there may be many other changes of different aspects of the present invention described above that are not provided in detail for the sake of brevity. Although the present invention has been described in detail with reference to the foregoing embodiments, those skilled in the art will appreciate that: the technical solutions disclosed in the above-mentioned embodiments can still be modified, or some of the technical features thereof can be replaced by equivalents; such modifications and substitutions do not depart the essence of the corresponding technical solutions from the scope of the technical solutions of various embodiments of the present invention.

The invention claimed is:

1. A line tube adapter assembly, comprising:
a housing provided with an accommodation cavity;
a connector comprising a base and a transmission line, wherein the base is accommodated in the accommodation cavity, and the transmission line is connected to one end of the base;
a line storage device accommodated in the accommodation cavity, wherein the line storage device is provided with an accommodation space configured to accommodate part of the transmission line;
and a line tube provided at one end of the line storage device away from the base, the line tube being connected to the housing;
further comprising a first limiting part and a second limiting part adapted to the first limiting part, wherein the first limiting part is located in the accommodation cavity and provided on an inner wall of the housing, and the second limiting part is provided on an outer wall of the base, the first limiting part and the second limiting part matching to circumferentially fix the connector and the housing;
wherein the first limiting part is a limiting protrusion extending from the inner wall of the housing to a center of the housing, the second limiting part is a limiting groove extending from the outer wall of the base to the center of the base and adapted to the limiting protrusion, and circumferential fixing is achieved between the housing and the connector through the matching of the limiting protrusion and the limiting groove; alternatively,
the first limiting part is a limiting groove extending from the inner wall of the housing to a direction away from the center of the housing, the second limiting part is a limiting protrusion extending from the outer wall of the base to a direction away from the center of the base and adapted to the limiting groove, and circumferential fixing is achieved between the housing and the connector through matching of the limiting groove and the limiting protrusion.

2. The line tube adapter assembly of claim 1, wherein the accommodation space is a through-hole extending through the line storage device from one end close to the base to one end away from the base.

3. The line tube adapter assembly of claim 2, wherein an outer wall of the line storage device is further provided with a side opening communicating with the accommodation space; the accommodation space always communicates with the side opening from one end close to the base to one end away from the base.

4. The line tube adapter assembly of claim 1, wherein the line storage device is integrally formed with the base.

5. The line tube adapter assembly of claim 1, wherein the inner wall of the housing is provided with a first plane, the first plane being the first limiting part, and the outer wall of the base is provided with a second plane, the second plane being the second limiting part, and the first plane is fitted with the second plane.

6. The line tube adapter assembly of claim 1, further comprising a third limiting part, and a fourth limiting part adapted to the third limiting part, wherein the third limiting part is located in the accommodation cavity and is provided on an inner wall of the housing, the fourth limiting part is provided on an outer wall of the line storage device, and the third limiting part and the fourth limiting part match to circumferentially fix the line storage device and the housing.

7. The line tube adapter assembly of claim 6, wherein the inner wall of the housing is provided with a third plane, the third plane being the third limiting part, and the outer wall of the line storage device is provided with a fourth plane, the fourth plane being the fourth limiting part, and the third plane is fitted with the fourth plane.

8. The line tube adapter assembly of claim 7, wherein the accommodation space is a through-hole extending through the line storage device from one end close to the base to one end away from the base,
the outer wall of the line storage device is further provided with a side opening communicating with the accommodation space, and the accommodation space always communicates with the side opening from one end close to the base to one end away from the base;
the side opening divides the fourth plane into two parts.

9. The line tube adapter assembly of claim 1, wherein the connector further comprises a communication port provided at one end of the base away from the transmission line, the communication port being connected to the transmission line.

10. The line tube adapter assembly of claim 1, wherein the housing is threadedly connected to the line tube.

11. The line tube adapter assembly of claim 10, wherein the inner side wall of the housing is provided with a centrally extending flange, one end of the base away from the transmission line abutting against the flange, one end of the base away from the flange abutting against or being fixed to the line storage device, and one end of the line tube extending into the accommodation cavity, abutting against the line storage device, and being threadedly connected to the housing.

12. An endoscope, comprising an endoscope body, and the line tube adapter assembly according to claim 1, wherein the transmission line is connected to the endoscope body.

* * * * *